United States Patent [19]

Biglin

[11] 4,250,737
[45] Feb. 17, 1981

[54] BATTERY POWERED GAS LEVEL INDICATOR

[75] Inventor: Timothy J. Biglin, Bristol, England

[73] Assignee: Horstmann Gear Group Ltd., Bath, England

[21] Appl. No.: 58,900

[22] Filed: Jul. 19, 1979

[30] Foreign Application Priority Data

Jul. 19, 1978 [GB] United Kingdom ............... 30325/78

[51] Int. Cl.³ ........................................... G01N 27/04
[52] U.S. Cl. ........................................ 73/23; 338/34; 422/98
[58] Field of Search ............... 73/23, 27 R; 338/34; 422/98

[56] References Cited

U.S. PATENT DOCUMENTS 4,147,513  4/1979  Bienkowski et al. .................... 73/23

FOREIGN PATENT DOCUMENTS 2313413  9/1974  Fed. Rep. of Germany ...... 324/71 SN

*Primary Examiner*—Donald O. Woodiel
*Attorney, Agent, or Firm*—Gilbert L. Wells

[57] ABSTRACT

A gas level indicator incorporates two Taguchi-type sensing elements, one of which is to receive air to be sampled and the other of which is insulated therefrom. A comparator circuit receives the outputs of the two elements, and an indicator actuated by the output of the circuit announces the result of the comparison. Preferably, both sensing elements are mounted in a single housing, and an elongated pipe and a fan or aspirator provided to form a probe for drawing air to be sampled from a remote position to the one element.

4 Claims, 2 Drawing Figures

BATTERY POWERED GAS LEVEL INDICATOR

This invention relates to a gas level indicator. There are indicators known which are fixed in position to indicate a dangerous increase in gas level in the ambient atmosphere. There are also portable quantitative indicators used, for example, to test for leaks on site. The present invention relates to the latter type of indicator or detector.

Such indicators as are known are both expensive and tend to be short-lived. In particular, existing indicators employ an element which is subject to poisoning and falsification by other gaseous media, for example lead-carrying petrol fumes.

It is an object of the invention to provide a portable indicator, preferably battery-powered, which is cheap, has a relatively long life, and is not subject to poisoning of the detector element.

Accordingly, the invention provides a gas level indicator incorporating two Taguchi-type gas sensing elements, one of which is to receive air to be sampled and the other of which is insulated therefrom, a comparator circuit receiving signals derived from the two elements, and an indicator actuated by the output of the circuit.

Such an indicator does not suffer the disadvantages of the known portable types, can be battery powered, and provides an accurate reading which eliminates the variables such as ambient pressure, temperature and atmospheric pollution which can otherwise lead to false readings.

In order that the invention shall be clearly understood, an exemplary embodiment thereof will now be described with reference to the accompanying drawings, of which:

Figure 1:
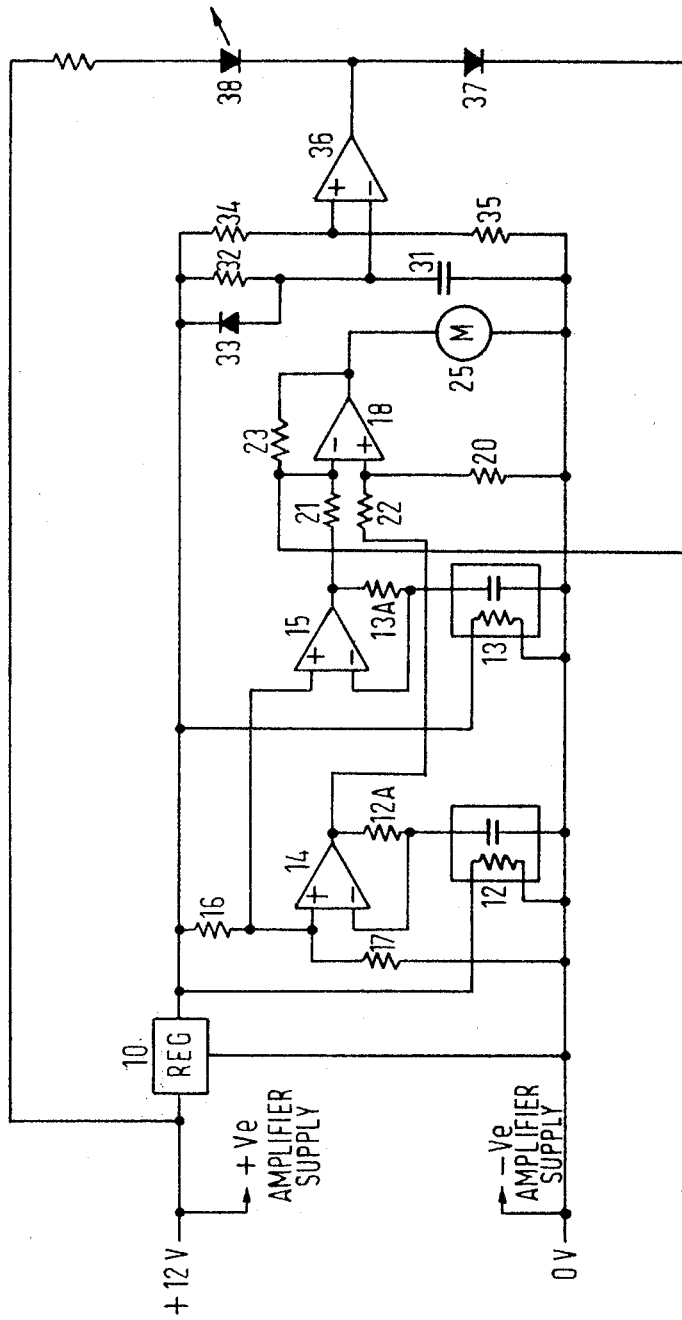
FIG. 1 shows the circuit diagram of a battery operated gas level indicator.

Referring now to the drawings, in the embodiment of FIG. 1 a 12 volt battery supply feeds the circuit. In order to provide a stable voltage for the detector circuits, a regulator 10 is employed. This directly feeds the heaters of two Taguchi-type gas sensing elements 12 and 13. The sensors themselves are in series respectively with resistors 12A, 13A. Two amplifiers 14, 15 receive a fixed proportion of this constant voltage supply, as determined by the voltage divider 16, 17.

Despite the changing resistance of each element 12, 13 the voltage across it is maintained constant by varying the total voltage output by the amplifiers across it and the series resistance 12A, 13A. These outputs are fed by resistors to a third amplifier 18. The resultant voltage from the two sensing elements is differentially amplified by this amplifier 18. The gain is conveniently set at unity by adjustment of the values of the resistors 20, 21, 22, 23. The output of the amplifier drives an analogue meter 25 to indicate gas concentration.

Figure 2:
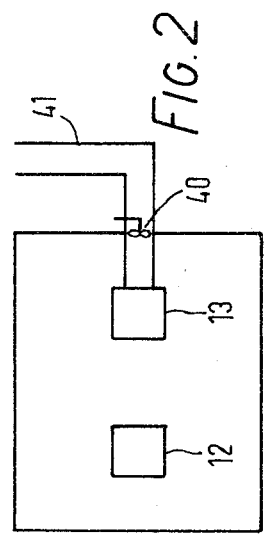
FIG. 2 is a schematic diagram of a housing for two sensing elements of the indicator.

One of the Taguchi-type gas sensing elements 12, 13 is used to monitor the ambient conditions, while the other element is positioned in air at or from a particular location to be tested, for example, a joint of a gas main. The said other element may be housed in a single casing with the rest of the parts of the indicator and supplied with a draught of air through a probe tube. FIG. 2 shows such an arrangement with two Taguchi-type sensing elements 12, 13 in a single casing or housing. Element 13 is suppied with air to be sampled by means of an elongated pipe 41 and a fan or aspirator element 40. Alternatively, the element may be itself housed at the end of a long probe so that it can be introduced into the location to be tested. However, this is a less advantageous arrangement since it carries the risk of a spark from the electrical connections which must be made along the probe to the element.

In either case, the effects of temperature, of humidity and of other gas contaminents are equalised for both probes, and a comparison can be made between the ambient situation and that at a particular narrow location required to be tested.

The circuit includes a further section designed to prevent a non-zero meter reading until the unit is ready for action, i.e., until the sensor heaters have warmed up. A capacitor 31 is charged via a resistor 32 and discharged via a diode 33 when the unit is switched off. The level of voltage across the capacitor is monitored relative to a voltage divider 34, 35 by a further amplifier 36. The output of this amplifier is high when the voltage across the capacitor is low. This high voltage is applied via a diode 37 to the amplifier 18, and thus keeps its output voltage low.

When the voltage across the capacitor 31 exceeds the voltage tapped, the output of the amplifier 36 changes from high to low. This reverse biases the diode 37, allowing the amplifier 18 to operate normally, and at the same time provides an indication that the meter reading can be trusted by illuminating a light emitting diode 38.

The analogue meter may if required be replaced by a simple on/off indicator.

I claim:

1. A gas level indicator incorporating two Taguchi-type gas sensing elements, one of which is to receive air to be sampled and the other of which is insulated therefrom, a comparator circuit receiving signals derived from the two elements, and an indicator actuated by the output of the circuit, wherein each sensing element is connected in series with a resistor, two amplifiers respectively supply a voltage across the element and its series resistor, and said voltage is in each case varied to maintain constant the partial voltage across the element alone, said voltage forming said signal in each case.

2. A gas level indicator incorporating two Taguchi-type gas sensing elements, one of which is to receive air to be sampled and the other of which is insulated therefrom, a comparator circuit receiving signals derived from the two elements, and an indicator actuated by the output of the circuit, wherein both sensing elements are mounted in a single housing, and an elongated pipe and a fan or aspirator are provided to form a probe for drawing air to be sampled to the one element.

3. A gas level indicator incorporating two Taguchi-type gas sensing elements, one of which is to receive air to be sampled and the other of which is insulated therefrom, a comparator circuit receiving signals derived from the two elements, and an indicator actuated by the output of the circuit, wherein a delay circuit is connected so as to block the output of the comparator circuit for an initial period after switching on matched to the warming up period of the sensing elements.

4. A gas level indicator as claimed in claim 3 wherein an indicator is included in the delay circuit which shows when said initial period has elapsed.

* * * * *